US005733474A

United States Patent [19]
Kagermeier et al.

[11] Patent Number: 5,733,474
[45] Date of Patent: Mar. 31, 1998

[54] THICKENED AQUEOUS PERACID COMPOSITIONS

[75] Inventors: Sonja Kagermeier, Deisenhofen, Germany; Christopher Revell; Sharon Lesley Wilson, both of Warrington, United Kingdom

[73] Assignee: Solvay Interox Limited, Warrington, England

[21] Appl. No.: 651,478

[22] Filed: May 22, 1996

Related U.S. Application Data

[63] Continuation of Ser. No. 140,024, filed as PCT/GB92/00820 May 6, 1992 published as WO92/19287 Nov. 12, 1992, abandoned.

[30] Foreign Application Priority Data

May 8, 1991 [GB] United Kingdom ............... 9109928

[51] Int. Cl.$^6$ ............... C01B 15/01; C01B 15/10; A61L 2/18
[52] U.S. Cl. ............... 252/186.25; 252/186.22; 252/186.26; 252/186.27; 252/186.28; 252/186.29; 422/28
[58] Field of Search ............... 252/186.22, 186.25, 252/186.26, 186.27, 186.28, 186.29; 422/28

[56] References Cited

U.S. PATENT DOCUMENTS

| | | | |
|---|---|---|---|
| 1,181,410 | 5/1916 | Schaidhauf | 252/186.27 |
| 2,590,856 | 4/1952 | Greenspan | 252/186.26 |
| 3,864,137 | 2/1975 | Van Bonin et al. | 106/603 |
| 3,996,151 | 12/1976 | Kirner | 252/186.27 |
| 3,996,152 | 12/1976 | Edwards et al. | 252/186.26 |
| 4,655,781 | 4/1987 | Hsieh et al. | 8/111 |
| 4,725,281 | 2/1988 | Stemlin et al. | 8/107 |
| 4,800,036 | 1/1989 | Rose et al. | 510/370 |
| 5,039,447 | 8/1991 | Reuben | 252/186.26 |
| 5,296,239 | 3/1994 | Colery et al. | 424/613 |

FOREIGN PATENT DOCUMENTS

| | | |
|---|---|---|
| 0 167 375 | 1/1986 | European Pat. Off. |
| 0 283 791 | 9/1988 | European Pat. Off. |
| 0 429 124 | 5/1991 | European Pat. Off. |

*Primary Examiner*—Joseph D. Anthony
*Attorney, Agent, or Firm*—Larson & Taylor

[57] ABSTRACT

Many aqueous compositions containing a peroxygen compound have a very low viscosity and thus easily run off non-horizontal surfaces. Particularly, when the peroxygen compound is a soluble peracid, the compositions are difficult to thicken successfully, because many commonly available thickening systems for aqueous media either fail to thicken them or are decomposed and/or decompose the peroxygen compound substantially during storage. The compositions, preferably containing a soluble peracid, are thickened with an alkali metal silicate, preferably sodium silicate, such as $Na_2O(SiO_2)_2$ used suitably in an amount of from about 2 to 6% of the composition and normally introduced in the form of a concentrated aqueous composition. The compositions may contain additionally an alkylammonium methosulphate. Preferred peracid solutions include dilute equilibrated peracetic acid solutions. The solutions when thickened to form a viscous liquid are suitable for disinfecting hard surfaces and when thickened to form a gel are suitable for suspension in an aqueous medium, for example in block form.

22 Claims, No Drawings

THICKENED AQUEOUS PERACID COMPOSITIONS

This application is a continuation of application Ser. No. 08/140,024 filed Jan. 25, 1994 now abandoned which is a 371 of PCT/GB 92/00820 filed May 6, 1992.

The present invention relates to thickened compositions and particularly to thickened peroxygen compositions.

During recent years, increasing attention has been paid by industry and the general public in Western Europe and North America to the environmental effects of the many substances that are employed in modern life. One of the classes of substances which have hitherto been widely employed comprises chlorine and oxychlorine derivatives thereof. Such compounds have been reported to generate under appropriate circumstances carcinogenic compounds and as a result, industry is seeking alternatives or replacements for such compounds in order to allay any residual public anxiety.

An alternative class of compounds comprises peroxygen compounds, of which one sub-class of especial interest comprises peracids which contain the moiety —CO—OOH. Peracids like hydrogen peroxide enjoy the substantial advantage of generating oxygen, either as such or in an active form during its deployment rather than chlorine or active chlorine species upon which environmentalists currently cast doubts. Furthermore, for a range of purposes such as disinfection, oxidation and bleaching, many of which are encountered domestically, peracids are more effective in general than hydrogen peroxide.

A number of the peracids are either liquid themselves or are produced conveniently in aqueous solution. Although such compositions are particularly appropriate for the treatment of or incorporation in liquid media, they are less appropriate for the treatment of solid surfaces, and particularly non-horizontal surfaces on account of the ability of liquid compositions to flow away from the point of contact. In consequence, and in order to extend the range of applications for peracids, it would be desirable to devise peracid-containing compositions that flowed less freely.

In principle, liquid compositions can be rendered less free-flowing by the incorporation of materials which thicken the liquid or introduce structure into the liquid. However, it is not practical to expect that substances which have hitherto been effective thickeners for other liquids would automatically be suitable for thickening liquid peracids or peracid solutions. This difficulty derives from the very same properties of the peracids that make them effective oxidising agents and bleaches. Interaction with thickeners during storage can result in the mutual decomposition of the peracid and the thickener, which in turn not only negates the beneficial effects of thickening, but also progressively removes the capability of the peracid to perform its desired task. It will be recognised that the problem is especially apparent in the case of peracids which are themselves either liquid or are present in solution. There is also a second important difficulty in attempting to thicken peracid solutions. The presence of the peracid and the corresponding carboxylic acid from which it can be derived, tends to significantly inhibit thickening. It is believed that the difficulty arises from interference of the peracid and/or carboxylic acid with aqueous structuring mechanisms which enable surfactants and like materials to thicken aqueous solutions. However, it will be understood that the instant invention does not depend upon the accuracy of the foregoing belief or explanation, but instead it relies upon the results actually demonstrated.

By comparison with soluble peracids, the problem can be somewhat diminished in the case of substantially insoluble solid peracids that are suspended in particulate form in aqueous media, because the peracid and the liquid constitute different physical phases that consequently minimise the extent of chemical interaction between them, and the thickening of the aqueous phase can occur with a lessened risk of interference from dissolved peracid species.

It will be understood that some other potential thickeners may initially or after a brief period of storage produce a much thickened composition, but one which is rather unstable, in that its viscosity falls away rapidly from its peak. Tests employing anionic polyacrylamides fell into that category.

It is an object of the present invention to seek to identify thickening substances which are capable of thickening peroxygen compositions. It is a second object of some preferred embodiments to identify materials capable of thickening soluble peracid compositions and obtain thereby compositions which are relatively stable during storage. It is a third object of a further set of embodiments of the present invention to identify materials which can thicken peroxygen compositions to produce viscous compositions which can be applied for disinfecting and/or cleansing purposes to non-horizontal surfaces.

According to the present invention there are provided aqueous compositions comprising a peroxygen compound at least partly in solution together with a thickener characterised in that the thickener comprises an alkali metal silicate in an amount sufficient to increase the viscosity to at least 100 cPs.

By the use of a thickening system of the present invention it is possible to obtain solutions which are thickened and in which the peroxygen compound decomposes by not more than an acceptable extent during storage. In other words; the composition enjoys both physical and chemical stability.

The invention thickening system is intended particularly for thickening soluble peracids. However, it will be recognised that the thickening system may alternatively be employed to thicken alternative peroxygen compositions, including compositions which are easier to thicken than soluble peracid compositions. In many embodiments, the peroxygen compound is organic. Thus, for example, the system is applicable to organic peroxides, ie organic compounds containing a —C—O—O—H or C—O—O—C— moiety, including alkyl, cycloalkyl or aryl peroxides, acyl peroxides, peroxycarbonates, and organic hydroperoxides and to compositions containing less or even poorly soluble peroxyacids such as those containing at least 8 carbons.

In particular, though, the system is applied to compositions containing soluble peracids, which may include low molecular weight aliphatic peroxyacids, for example containing up to 6 carbon atoms, of which especially preferred examples comprise peracetic acid and perpropionic acid. Other examples include perbutyric acid, persuccinic acid and perglutaric acid. The compositions may alternatively include soluble aromatic peroxyacids, such as monoperphthalic acid, or sulphoperbenzoic acid. A mixture of peracids may be employed, if desired.

The peroxygen compound, such as the peracid, may be present in a wide range of concentrations, for example up to about 40%. For any component, % herein is by weight based on the total weight of the composition, unless specifically stated otherwise. The lower limit is at the discretion of the user, but is normally not below about 0.1%. The invention is particularly applicable to ready to use compositions containing a low concentration of active peroxygen compound, and for example compositions intended for application for cleansing and/or disinfecting purposes to hard surfaces and particularly to non-horizontal surfaces. Such dilute compositions typically contain from 0.25 to about 5% by weight of an organic peroxygen compound, preferably a peracid, for example peracetic acid and in a number of practical embodiments the peroxygen compound content will be from about 0.5 to 2%. It will be recognised that such compositions may contain a significant concentration of hydrogen peroxide, which may, for example, comprise from about 1 to 12% of the composition, and in a number of embodiments from 3 to 10%.

The peracid compositions, and particularly those containing aliphatic peracids are often conveniently derived by oxidation of the corresponding aliphatic carboxylic acid with aqueous hydrogen peroxide, and will often contain residual amounts of both the carboxylic acid and hydrogen peroxide. Thus, the compositions may contain up to 40% of the corresponding carboxylic acid and up to 40% hydrogen peroxide, with a minimum water content usually of 20%. However, in dilute peracid solutions, the concentration of the carboxylic acid and of hydrogen peroxide each tend to be selected in the range from about 1 to 12%. The total concentration of carboxylic acid plus percarboxylic acid is often from 3 to 20% and in many instances from 3 to 15%. It is often convenient to restrict the concentration of hydrogen peroxide to no greater than 7%. In many preferred compositions, equilibrium amounts of carboxylic acid, percarboxylic acid and hydrogen peroxide are present.

The thickening system of the present invention comprises an alkali metal silicate. The amount of silicate to employ depends on how thick a composition is desired. By appropriate adjustment of the silicate concentration, it is possible to obtain a wide range of compositions. At one extreme, the compositions remain easily pourable, but distinctly more viscous than the corresponding composition without added silicate. At the other extreme, the compositions are gelled, forming as product that is in effect a solid. The silicate concentrations tend to be selected in the region of at least 2% by weight in order to obtain compositions having viscosities of about 300 cPs or higher and in many embodiments the concentration is not greater than 6% by weight.

The silicate is usually sodium silicate, on account of its widespread availability at a reasonable cost, but other silicates such as potassium or lithium may be employed instead of all or part of the sodium silicate.

Alkali metal silicates are usually represented by the formula $(M_2O) \cdot (SiO_2)_m$ in which M represents an alkali metal and m the mole ratio of alkali metal oxide, eg soda to silica. Silicates are obtainable in the range of m=about 1 to about 4. Particularly effective results have been obtained in the region of m=2. It will be recognised that the viscosity of the composition is to some extent dependent upon the mole ratio of alkali metal oxide to silica. For introduction of the same concentration of alkali metal silicates, there is a tendency for the viscosity to decrease as the mole ratio m increases.

It is desirable to select relatively pure alkali metal silicates and particularly samples which are not contaminated with an excessive residue of transition metals. By so doing, it is possible to maintain peroxygen compound stability. For example, when thickening peracid compositions, it has been found desirable to use a silicate that has been supplied as or purified to an iron content of not greater than about 20 ppm. Naturally, though, if it is anticipated that contaminating metal ions may be present that would promote peroxygen compound decomposition, it is desirable to incorporate one or more chelating stabilisers, such as are described subsequently herein.

According to a second aspect of the present invention there is provided a process for preparing a thickened composition by introducing an effective amount of an alkali metal silicate into an aqueous composition containing a peroxygen compound and agitating the mixture.

The silicates are conveniently introduced into the composition in the form of an aqueous solution, preferably concentrated and up to saturated solution and for example containing between about 30 and 50% by weight alkali metal silicate, in order to assist even distribution and mixing of the silicate with the peroxygen compound solution. Direct introduction of solid silicate is not recommended.

The physical state of the composition may also be modified by the presence of one or more viscosity modifiers. By so doing, it is possible to fine tune, to at least some extent, the ability of the composition to be poured.

The pH of the composition is a further factor affecting the viscosity attained by a thickened composition during storage and the rate at which thickening occurs in the present invention. In particular, it is desirable to employ a pH of at least 1, approximately, so as to encourage thickening to occur and in practice the pH is normally not higher than about 4.5. As a generalised expression of a trend, thickening becomes progressively quicker and easier to obtain as the pH of the solution is higher. A preferred pH range for the compositions comprise from about pH 3 to 4.5. Advantageously, many compositions such as dilute peracetic acid compositions attain that range without any further adjustment.

It will be understood that the thickened compositions of the present invention tend to thicken over a period of time, rather than attain the maximum thickness quickly. Advantageously, this means that the compositions normally still be readily handled using conventional bottling or liquid transporting equipment for a reasonable period after introduction of the thickening system.

The compositions may include one or more stabilisers for peracids and/or hydrogen peroxide so as to encourage the chemical stability of the thickened products. Known stabilisers for peroxy compounds include aminopolycarboxylic acids, such as EDTA and DTPA, or N-heterocyclic aromatic carboxylic acids such as quinolinic acid, picolinic acid and dipicolinic acid. Particularly effective stabilisers comprise organic polyphosphonic acids, including hydroxyethylidene-diphosphonic acid and aminopolymethylene phosphonic acids. The latter often satisfy the general formula:

$X_2N$—(—$CHR$—$CHR$—$NX$—$)_n$—$NX_2$ in which X represents —$CH_2$—$PO_3H_2$ R represents H or the two R substituents combine to complete a cyclohexane ring, and n is an integer from 1 to 3. Examples of the formula include ethylenediaminetetra-(methylene phosphonic acid), diethylenetriaminepenta-(methylene phosphonic acid) and cyclohexanediaminetetra-(methylene phosphonic acid).

In addition to the foregoing components, the composition may also contain one or more surfactants, for example amine oxides, and additionally or alternatively, one or more perfumes and/or dyes, preferably selected at least partly on the basis of resistance to oxidation.

The compositions of the present invention can be made by introducing the selected amount of the alkali metal silicate, preferably in concentrated aqueous solution, into an aqueous precursor composition containing essentially water and the peroxygen compound, such as an aqueous solution of peracid, which solution can optionally contain any residual amounts of the corresponding carboxylic acid and hydrogen peroxide, and agitating the resultant mixture to distribute the thickener substantially evenly through the mixture. The silicate solution introduced preferably has a concentration of at least 30% w/w up to a saturated solution.

Desirably, the pH of the solution is measured and adjusted, if necessary, by introduction of the appropriate choice from a mineral acid if the solution is insufficiently acid or an alkali if the solution is too acid. The process can be conducted at any convenient temperature, for example at the prevailing ambient temperature which is typically in the range of from 10° to 35°. Alternatively, the mixture may be gently heated to not higher than about 50° C. so as to encourage rapid distribution of the thickener and the mixture thereafter permitted to cool to ambient.

Some of the compositions of the present invention, and particularly those having a viscosity in the region of about 200, preferably about 250, to 600 cPs are intended for application domestically to surfaces, such as non-horizontal surfaces, which it is desired to disinfect and clean, thereby taking advantage of the disinfectant properties of the peroxygen compound, especially the peracid and the cleansing properties of the detergents. The peroxygen compositions in solid form may be incorporated in particulate or granular washing or disinfecting compositions or dispersed in blocks or bars. Such blocks or bars may also incorporate substances such as waxes, either natural or synthetic polymers or very poorly soluble aliphatic carboxylic acids or poorly soluble derivatives and/or mixtures thereof which can regulate and retard the extent of contact between the peroxygen compound composition and for example a liquid medium such as flushing toilet water.

Accordingly, a third aspect of the present invention comprises the use the aforementioned invention compositions for disinfecting and cleansing by applying the composition to a hard surface and permitting contact to be maintained until at least some disinfection has occurred.

The invention compositions may be applied using conventional means and will also take into account the physical state of the composition, particularly whether it is a viscous pourable liquid or a gel. Thus, in its simplest, the compositions may be poured or smeared onto a distributor such as a cloth or sponge and applied to a receiving surface by passage of distributor across the surface. Alternatively, the compositions which have a sufficiently low viscosity for them to be pourable, may be forced through a distributing nozzle directly onto the receiving surface, for example by squeezing a resilient deformable storage container. Compositions in gel form may be applied by a spatula or like article or as indicated previously by incorporation in a host composition or block.

The surfaces onto which the compositions may be applied are often domestic and especially in the kitchen and other locations in which micro-organisms may be found. Suitable receptive surfaces are usually made from wood, glass, ceramics, plastic laminates and metal, and including work surfaces, sinks, pipework, walls, floors, and especially toilet bowls. It will be recognised, though, that similar potentially infected surfaces may be found in non-domestic situations, such as in commercial kitchens, food processing apparatus or containers or brewery or distillery vessels or hospitals or in animal or poultry-rearing establishments or in glass houses or other areas where the maintenance of hygienic conditions is important. The present invention includes the use of invention compositions in such non-domestic situations.

The compositions may subsequently be removed from the surfaces by water washing, possibly applied using a cloth, sponge or like article.

A further use for a gelled composition is to form it into a block and suspend it, either as such or within a permeable container, within a liquid medium that it is desired to disinfect, such as process water, industrial circulating water or domestically the water supply to a toilet.

Having described the invention in general terms, specific embodiments thereof will now be described in greater detail by way of example only.

For use in the Examples, a batch of silicate solution was made dissolving sodium silicate powder having an $SiO_2:Na_2O$ mole ratio of 2:1, obtainable from Joseph Crossfield under their trade name Crystal C Powder to a concentration of 40%. The solution contained on analysis<10 ppm Fe.

EXAMPLE 1

In this Example, a thickened peracid composition was made by stirring at laboratory ambient temperature (about 22° C.), the aforementioned silicate solution (5 g) and hydroxyethylidene-diphosphonic acid available under the Trademark DEQUEST grade 2010 (100 ppm) into a solution of peracetic acid available from Interox Chemicals (100 g) which analysed as peracetic acid (1%) acetic acid (9%) hydrogen peroxide (6%) and the balance water. The resultant composition had a pH of about 3.5, which fell to about pH 3.3 during storage. After 16 weeks, the composition had a viscosity measured using a Brookfield synchroelectric viscometer of 400 cPs. The available oxygen (Avox) of the composition was measured on production and after 16 weeks storage at 22° C. using a conventional ceric sulphate/sodium thiosulphate technique. By comparing the two analyses, it was found that the composition had retained 69% of its Avox.

EXAMPLE 2

In this Example, Example 1 was repeated, but employing 7 g of the sodium silicate solution. The resultant composition had a pH of 3.5 rising to pH 4 after storage for 20 days and a viscosity of about 1500 cPs after 12 days. The composition had become solidified during storage for 20 weeks at 22° C., by which time it had retained 86% of its Avox.

EXAMPLE 3

In this Example, Example 1 was repeated, but employing 13 g of the sodium silicate solution. The resultant composition had a pH of 3.9 rising to pH 4.0 after storage for 20 days and a viscosity of over 80,000 cPs after 16 weeks. The composition retained 47% of its Avox after 16 weeks storage at 22° C.

EXAMPLE 4

In this Example, Example 4 was repeated, but employing in addition concentrated sulphuric acid, 1.2 ml. The resultant composition had a pH of 1.2, and a viscosity of about 1400 cPs after 16 weeks. The composition retained 74% of its Avox after 16 weeks storage at 22° C.

EXAMPLE 5

In this Example, Example 3 was repeated, additionally incorporating an alkylammonium methosulphate (2 g) available from Stepan under their trademark STEPANQUAT F.

The resultant composition had a viscosity of 22,000 cPs after 16 weeks storage at 22° C. and had retained 99% of its Avox.

EXAMPLE 6

In this Example, Example 3 was repeated, additionally incorporating an amine oxide (2 g). After 16 weeks storage at 22° C., the composition had a viscosity of 3000 cPs and had retained 72% of its Avox.

We claim:

1. In a process for disinfection of a substrate, comprising contacting the substrate with a storage stable aqueous acidic composition having a pH>1 comprising a soluble peroxygen compound in solution together with a thickener, the improvement wherein the thickener comprises an alkali metal silicate, the alkali metal silicate being present in the composition in an amount sufficient to increase the viscosity of the composition to at least 100 cPs and such that the composition is distinctly more viscous than the composition without the added silicate.

2. A process according to claim 1, wherein the peroxygen compound comprises peracetic acid.

3. In a storage stable aqueous acidic composition having a pH>1 comprising a soluble peroxygen compound in solution together with a thickener, the improvement wherein the thickener comprises an alkali metal silicate, the alkali metal silicate being present in the composition in an amount sufficient to increase the viscosity of the composition to at least 100 cPs and such that the composition is distinctly more viscous than the composition without the added silicate.

4. A thickened composition according to claim 3 wherein the peroxygen compound comprises a peracid.

5. A thickened composition according to claim 4 wherein the peracid is soluble.

6. A thickened composition according to claim 5 wherein the peracid comprises peracetic acid.

7. In a storage stable aqueous acidic composition having a pH>1 comprising a soluble peracetic acid together with a thickener, the improvement wherein the thickener comprises an alkali metal silicate having the formula $(M_2O)\cdot(SiO_2)_m$ in which m is about 2, the alkali metal silicate being present in the composition in an amount sufficient to increase the viscosity of the composition in an amount sufficient to increase the viscosity of the composition to at least 100 cPs and such that the composition is distinctly more viscous than the composition without the added silicate.

8. A thickened composition according to claim 4 or 7 containing from 0.25 to 5% w/w peracid.

9. A thickened composition according to claim 5, 6, or 7, further containing carboxylic acid and hydrogen peroxide each in an amount of from about 1 to 12% w/w.

10. A thickened composition according to claim 9 wherein the combined amount of peracid and carboxylic acid is in the range of from 3 to 15%.

11. A thickened composition according to claim 3, 4, 5, or 6 wherein the alkali metal silicate has the formula $(M_3O)\cdot(SiO_2)_m$ in which m is about 2.

12. A thickened composition according to claim 3, 4, 5, 6, or 7 wherein the amount of alkali metal silicate employed is in the range of from 2 to 6% w/w of the composition.

13. A thickened composition according to claim 3, 4, 5, 6, or 7 wherein the alkali metal silicate is sodium silicate.

14. A thickened composition according to claim 3, 4, 5, 6, or 7 wherein the silicate employed has an impurity content of no greater than 20 ppm iron calculated as Fe.

15. A thickened composition according to claim 3, 4, 5, 6, or 7 wherein the composition after thickening has a pH in the range of from pH 3 to pH 4.5.

16. A thickened composition according to claim 3, 4, 5, 6, or 7 wherein sufficient alkali metal silicate is employed to attain a viscosity after storage for 16 weeks of from about 250 to 600 cPs.

17. A thickened composition according to claim 3, 4, 5, 6, or 7 wherein sufficient alkali metal silicate is employed to solidify the composition.

18. A thickened composition according to claim 3, 4, 5, 6, or 7 further containing an alkylammonium methosulphate.

19. A thickened composition according to claim 3, 4, 5, 6, or 7 further containing a stabilizer for peroxygen compounds.

20. A process for preparing a storage stable thickened composition which comprises introducing an alkali metal silicate into an aqueous acidic composition having a pH >1 and containing a soluble peroxygen compound, the alkali silicate being introduced in an amount sufficient to increase the viscosity of the composition to at least 100 cPs and such that the composition is distinctly more viscous than the composition without the added silicate, and agitating the mixture.

21. A process according to claim 20 wherein the alkali metal silicate is introduced in the form of a concentrated aqueous solution.

22. A process according to claim 20 wherein the alkali metal silicate is introduced in the form of an aqueous solution having a silicate concentration of from 30% w/w to a saturated solution.

* * * * *